United States Patent
Yada et al.

(10) Patent No.: US 7,786,323 B2
(45) Date of Patent: Aug. 31, 2010

(54) METHOD FOR COLLECTING (METH)ACROLEIN OR (METH)ACRYLIC ACID AND COLLECTING DEVICE FOR THE SAME

(75) Inventors: Shuhei Yada, Minato-ku (JP); Yasushi Ogawa, Yokkaichi (JP); Kenji Takasaki, Yokkaichi (JP); Yoshiro Suzuki, Yokkaichi (JP); Kimikatsu Jinno, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/434,164

(22) Filed: May 16, 2006

(65) Prior Publication Data

US 2006/0211886 A1 Sep. 21, 2006

Related U.S. Application Data

(63) Continuation of application No. PCT/JP2004/014639, filed on Oct. 5, 2004.

(30) Foreign Application Priority Data

Nov. 28, 2003 (JP) .............................. 2003-399217

(51) Int. Cl.
*B01D 47/00* (2006.01)
(52) U.S. Cl. .................. 562/600; 568/492; 95/237; 95/238; 95/240; 95/211; 96/290
(58) Field of Classification Search ........... 95/237–238, 95/240, 210–211; 96/413, 290, 322; 562/600; 568/492
See application file for complete search history.

(56) References Cited

U.S. PATENT DOCUMENTS

| | | | | | |
|---|---|---|---|---|---|
| 2,410,215 | A | * | 10/1946 | Houghton | .................... 239/515 |
| 3,334,470 | A | * | 8/1967 | Huppke | ........................ 95/216 |
| 3,433,840 | A | | 3/1969 | Shima et al. | |
| 3,498,028 | A | * | 3/1970 | Trouw | .......................... 96/306 |
| 3,605,388 | A | * | 9/1971 | Zuiderweg et al | ............. 96/305 |
| 4,266,951 | A | * | 5/1981 | Calvert | ........................ 95/216 |
| 4,317,926 | A | | 3/1982 | Sato et al. | |
| 4,350,665 | A | * | 9/1982 | Hashimoto et al. | .......... 422/191 |

(Continued)

FOREIGN PATENT DOCUMENTS

DE 19631332 A1 * 11/1997

(Continued)

OTHER PUBLICATIONS

U.S. Appl. No. 11/547,864, filed Oct. 6, 2006, Ogawa et al.

*Primary Examiner*—Duane Smith
*Assistant Examiner*—Ives Wu
(74) *Attorney, Agent, or Firm*—Oblon, Spivak, McClelland, Maier & Neustadt, L.L.P.

(57) ABSTRACT

(Meth)acrolein or (meth)acrylic acid is collected by bringing a reaction gas (1) containing (meth)acrolein or (meth)acrylic acid obtained through a vapor-phase catalytic oxidation reaction into contact with an aqueous solution as a collecting solvent in a collecting tower main body (2). The reaction gas (1) is supplied to the collecting tower main body (2) from two nozzles (2*c*) facing each other, and is caused to collide in the collecting tower main body (2). According to the present invention, (meth)acrolein or (meth)acrylic acid can be efficiently collected from a gas containing (meth)acrolein or (meth)acrylic acid while preventing polymerization.

6 Claims, 5 Drawing Sheets

U.S. PATENT DOCUMENTS

| | | | | |
|---|---|---|---|---|
| 4,647,212 A | * | 3/1987 | Hankison | 366/165.5 |
| 4,687,495 A | * | 8/1987 | Maddox | 95/258 |
| 4,741,885 A | * | 5/1988 | Herbort et al. | 422/197 |
| 5,240,482 A | * | 8/1993 | Sung | 96/235 |
| 6,294,056 B1 | * | 9/2001 | Matsumoto et al. | 203/90 |
| 6,641,700 B1 | | 11/2003 | Matsumoto et al. | |
| 6,649,028 B2 | * | 11/2003 | Sakamoto et al. | 203/98 |
| 6,667,419 B1 | | 12/2003 | Matsumoto et al. | |
| 7,014,736 B2 | * | 3/2006 | Matsumoto | 203/8 |
| 2004/0244382 A1 | * | 12/2004 | Hagen et al. | 60/775 |

FOREIGN PATENT DOCUMENTS

| | | | |
|---|---|---|---|
| GB | 2 024 201 A | | 1/1980 |
| GB | 2024201 A | * | 1/1980 |
| GB | 2024201 A | * | 1/1980 |
| JP | 51-2675 | | 1/1976 |
| JP | 54-141721 | | 11/1979 |
| JP | 9-157213 | | 6/1997 |
| JP | 2000-254403 | | 9/2000 |
| JP | 2001-19655 | | 1/2001 |
| SU | 1169528 A | | 7/1985 |
| ZA | 20003215 | | 6/2000 |

* cited by examiner

METHOD FOR COLLECTING (METH)ACROLEIN OR (METH)ACRYLIC ACID AND COLLECTING DEVICE FOR THE SAME

CROSS-REFERENCE TO A RELATED APPLICATION

The present application is a continuation of International Application PCT/JP04/014639, filed Oct. 5, 2004, which claims priority to Japanese Patent Application No. 2003-399217, filed Nov. 28, 2003.

TECHNICAL FIELD

The present invention relates to a method for collecting (meth)acrolein or (meth)acrylic acid, and more specifically to a method for collecting (meth)acrolein or (meth)acrylic acid using a solvent for collecting (meth)acrolein or (meth)acrylic acid from a gas containing (meth)acrolein or (meth)acrylic acid obtained through vapor-phase catalytic oxidation of propylene, propane or isobutylene using molecular oxygen.

BACKGROUND ART (Meth)acrolein or (meth)acrylic acid is usually produced using a multitube reactor through a vapor-phase catalytic oxidation reaction of propylene, propane or isobutylene in the presence of a mixed oxide catalyst using molecular oxygen or a molecular oxygen-containing gas. (Meth)acrolein or (meth)acrylic acid can be obtained from a resulting reaction gas through a collecting method using a collecting solvent.

Example of a conventional method for collecting (meth)acrolein or (meth)acrylic acid from a gas containing (meth)acrolein or (meth)acrylic acid using a solvent includes collecting method using water or an aqueous solution as a collecting solvent. Example of such a collecting method includes a known technique involving cooling a large volume of a gas by adjusting a composition of an aqueous solution used for collecting, to thereby collect (meth)acrolein or (meth)acrylic acid (see JP 09-157213 A, for example).

The conventional method for collecting (meth)acrolein or (meth)acrylic acid from a gas containing (meth)acrolein or (meth)acrylic acid using an aqueous solution has problems in that (meth)acrolein or (meth)acrylic acid was not even partially collected and was discharged along with a reaction gas because of a very large volume of the reaction gas supplied to a collecting device.

Meanwhile, example of the method for collecting (meth)acrolein or (meth)acrylic acid using a solvent includes another known technique involving cooling a large volume of a gas by adjusting a shape of or arranging method for internals of a collecting device, to thereby collect (meth)acrolein or (meth)acrylic acid (see JP 2001-019655 A, for example).

The method employing high performance packing for internals of the collecting device is not sufficient because when a collecting tower is used as the collecting device, an increase of acrylic acid distilled to a top of the collecting tower due to operational fluctuation of the tower easily causes clogging through polymerization of acrylic acid.

DISCLOSURE OF THE INVENTION

The present invention has been made in view of the above-mentioned problems, and an object of the present invention is to provide a method and device for efficiently collecting (meth)acrolein or (meth)acrylic acid from a gas containing (meth)acrolein or (meth)acrylic acid using a collecting device while preventing polymerization.

The inventors of the present invention have conducted various studies for solving the problems, and have found out that, upon collecting, a supply method for a reaction gas flowing into the collecting device is closely related to an efficiency of the collecting device and to prevention of polymerization.

That is, the present invention provides a method for collecting (meth)acrolein or (meth)acrylic acid, including the step of bringing a reaction gas containing (meth)acrolein or (meth)acrylic acid obtained through a vapor-phase catalytic oxidation reaction of one or both of (A) propane, propylene or isobutylene and (B) (meth)acrolein, and molecular oxygen or a molecular oxygen-containing gas into contact with a solvent in a collecting device to collect (meth)acrolein or (meth)acrylic acid in the solvent, in which the reaction gas is supplied to the collecting device from a plurality of positions, and is caused to collide in the collecting device.

The present invention provides a collecting device for collecting (meth)acrolein or (meth)acrylic acid by bringing a reaction gas containing (meth)acrolein or (meth)acrylic acid obtained through a vapor-phase catalytic oxidation reaction of one or both of (A) propane, propylene or isobutylene and (B) (meth)acrolein, and molecular oxygen or a molecular oxygen-containing gas into contact with a solvent, the collecting device including a contact portion where the reaction gas is brought into contact with the solvent, a plurality of reaction gas supply devices for supplying the reaction gas to the contact portion, and solvent supply device for supplying the solvent to the contact portion, in which the plurality of reaction gas supply devices supply the reaction gas to cause a collision of the reaction gas in the contact portion.

BEST MODE FOR CARRYING OUT THE INVENTION

Figure 1:
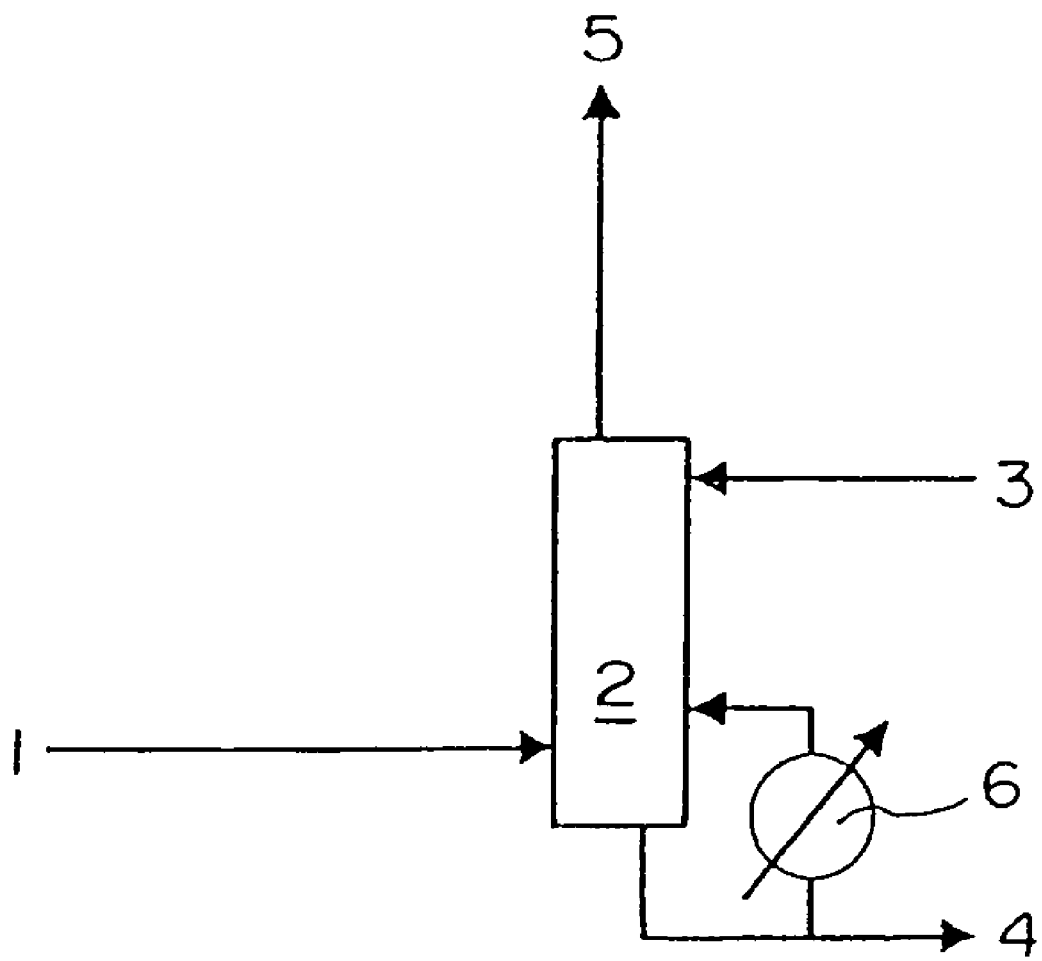
FIG. 1 is a system diagram showing an embodiment of a collecting device according to the present invention.

A method for collecting (meth)acrolein or (meth)acrylic acid of the present invention includes the step of bringing a reaction gas containing (meth)acrolein or (meth)acrylic acid obtained through a vapor-phase catalytic oxidation reaction of one or both of (A) propane, propylene or isobutylene and (B) (meth)acrolein, and molecular oxygen or a molecular oxygen-containing gas into contact with a solvent in a collecting device to collect (meth)acrolein or (meth)acrylic acid in the solvent.

In the present invention, (meth)acrolein refers to acrolein or methacrolein, and (meth)acrylic acid refers to acrylic acid or methacrylic acid. Industrially, a reaction gas containing (meth)acrolein or (meth)acrylic acid in the present invention is usually obtained by oxidizing propane, propylene, isobutylene, and/or (meth)acrolein in the presence of a solid catalyst using molecular oxygen, that is, through so-called vapor-phase catalytic oxidation.

Hereinafter, the descriptions will be referred to acrylic acid as a typical example.

Examples of a general production method for acrylic acid include: a method involving reacting propylene with a molecular oxygen containing gas such as air in the presence of a molybdenum oxide-based solid oxidation catalyst to produce acrylic acid directly (one-stage method: see JP 07-053448 A, for example); and a method involving reacting propylene with molecular oxygen in the presence of a molybdenum oxide-based solid oxidation catalyst in a first reaction zone to obtain acrolein, and reacting acrolein with molecular oxygen in the presence of a molybdenum oxide-based solid oxidation catalyst in a second reaction zone to produce acrylic acid (two-stage method: see JP 47-010614 A and JP 63-093747 A, for example). The gas obtained through those methods can be preferably used as a reaction gas in the present invention.

In the present invention, a reaction gas of acrylic acid obtained as described above is a gas containing acrylic acid. Thus, in order to separate acrylic acid from the reaction gas, acrylic acid is brought into contact with a solvent to collect acrylic acid, and acrylic acid is obtained as an acrylic acid-containing solution.

The reaction gas contains acrylic acid produced through vapor-phase catalytic oxidation at high temperatures of usually about 250 to 300° C., but is preferably cooled to 140 to 250° C., particularly 170 to 220° C. before being supplied to a collecting tower.

A solvent used in the collecting method of the present invention (hereinafter, the solvent may also be particularly referred to as "collecting solvent") is not particularly limited, but is preferably an aqueous solution containing 80 wt % or more water, more preferably an aqueous solution containing 85 wt % or more water. Components of the collecting solvent except water include formaldehyde, formic acid, acetic acid, and acrylic acid. Such aqueous solutions may be used as the collecting solvents for improving a collection efficiency of acrylic acid.

A collecting device used for the collecting method of the present invention is not particularly limited so long as the device allows gas-liquid contact and recovery of the liquid, but a tower-type collecting device having a collecting tower is preferred. The collecting tower is not particularly limited, and examples thereof include a tray collecting tower and a packed collecting tower.

Specific examples of trays include bubble cap trays each having a downcomer, perforated-plate trays, valve trays, SUPERFRAC trays, MAX-FRAC trays, and dual flow trays without downcomers.

As packing, examples of structured packing include: SULZER PACKING available from Sulzer Brothers Ltd.; SUMITOMO-SULZER PACKING available from Sumitomo Heavy Industries, Ltd.; MELLAPAK available from Sumitomo Heavy Industries, Ltd.; GEM-PAK available from Koch-Glitsch, LP; MONTZ-PAK available from Julius Montz GmbH; GOOD ROLL PACKING available from Tokyo Tokushu Kanaami K. K.; HONEYCOMB PACK available from NGK Insulators, Ltd.; IMPULSE PACKING available from Nagaoka International Corporation; and MC PACK available from Mitsubishi Chemical Engineering Corporation.

Examples of random packing include: INTALOX SADDLES available from Norton; TELLERETT available from Nittetsu Chemical Engineering Ltd.; PALL RINGS available from BASF Aktiengesellschaft; CASCADE MINI-RING available Mass Transfer Ltd.; and FLEXI RINGS available from JGC Corporation.

The types of the trays and packing are not limited in the present invention, and one or more types thereof can be used in combination as generally used.

In the present invention, the reaction gas is supplied to the collecting device from a plurality of positions and is caused to collide in the collecting device.

The number of supply positions of the reaction gas is not particularly limited if the number thereof is 2 or more. The number thereof is preferably 2 to 8, more preferably 2 to 4 from the viewpoints of productivity, operational ease, equipment cost, and the like.

The reaction gas is supplied to the collecting device from the plurality of positions to collide in the collecting device. Thus, the reaction gas is dispersed in the collecting device with enhanced contact between the collecting solvent and the reaction gas without use of a regulating member such as an impingement plate or a baffle board for regulating a gas flow by being into contact with the gas. Further, the reaction gas is dispersed without the regulating member, thereby preventing formation of a polymerized product on the regulating member.

In the present invention, all the reaction gas supplied from the plurality of positions preferably collides in the collecting device. However, all the reaction gas supplied form the plurality of positions needs not collide if the reaction gas is sufficiently dispersed in the collecting device. Furthermore, in the present invention, all the reaction gas supplied from the plurality of positions preferably collides at one place. However, all the reaction gas supplied form the plurality of positions may collide at a plurality of positions in the collecting device if the reaction gas is sufficiently dispersed in the collecting device.

The reaction gas may collide in the collecting device by supplying the reaction gas from the plurality of positions toward a one arbitrary place in the collecting device. The collision of the reaction gas in the collecting device may be caused by: fixing a supply direction of the reaction gas and adjusting a supply amount thereof in accordance with the supply direction; fixing a supply amount of the reaction gas and adjusting a supply direction thereof in accordance with the supply amount; or adjusting a supply amount or supply direction of the reaction gas in accordance with the supply direction or supply amount of the reaction gas.

In the present invention, when an amount (Q/N) in which all the amount (Q) of the reaction gas supplied to the collecting device is devided by the number (N) of the positions for supplying the reaction gas in the reaction device is defined as a reference, a reaction gas flow rate error among the plurality of positions is preferably ±10% or less for improving dispersibility of the reaction gas in the collecting device. The flow rate can be controlled by, for example: use of distribution device such as a header (distributor) or flow rate adjusting device such as a fan or a valve; and a combination of diameters of individual nozzles for supplying the reaction gas to the collecting device and a flow rate of the reaction gas flowing through each of the nozzles. Such control of the flow rate is more effective for a case where the reaction gas is caused to collide in an arbitrary place substantially equidistant from the plurality of positions in the collecting device.

In the present invention, all the reaction gas supplied to the collecting device from the plurality of positions preferably collides directly at one place for enhancing the dispersibility of the reaction gas in the collecting device and preventing formation of a polymerized product due to contact between a member of the collecting device such as the regulating member and the reaction gas.

In the present invention, when the collecting device has a circular cross sectional shape as the above-mentioned tower-type collecting device, all the reaction gas supplied to the collecting device from the plurality of positions preferably collides directly at a center of the collecting device for enhancing the dispersibility of the reaction gas in the collecting device, enhancing contact between the reaction gas and the collecting solvent, and preventing the above-mentioned formation of a polymerized product.

The collecting device of the present invention is used for collecting (meth)acrolein or (meth)acrylic acid in a collecting solvent by bringing the reaction gas into contact with the collecting solvent. The collecting device includes: a contact portion where the reaction gas is brought into contact with the collecting solvent; the plurality of reaction gas supply devices for supplying the reaction gas to the contact portion; and solvent supply device for supplying the collecting solvent to the contact portion.

The contact portion is not particularly limited so long as the portion allows gas-liquid contact. Example of the contact portion includes a showering device. However in the present invention, the contact portion preferably has a circular cross sectional shape for enhancing the dispersibility of the reaction gas, and more preferably employs the tray collecting tower or the like described above.

The plurality of reaction gas supply devices are not particularly limited so long as the reaction gas supplied to the contact portion from each of the reaction gas supply devices is supplied to collide in the contact portion. Each of the reaction gas supply devices is not particularly limited so long as a gas is supplied to a desired direction. Each of the reaction gas supply devices may be: a device capable of adjusting a supply amount of the reaction gas supplied; or a device capable of changing a supply direction of the reaction gas. Examples of each of the reaction gas supply devices include: a spray capable of changing a direction of a spray port and reducing a diameter of the spray port; and a nozzle fixed to a contact portion.

The nozzle used in the present invention is the same as a nozzle generally defined. To be specific, the nozzle refers to a tube connected to an equipment main body and includes from the equipment main body to a first flange of the tube. The nozzle is provided by welding or screwing. In the present invention, nozzles selected each have an appropriate diameter for supplying a reaction gas to a contact portion at a sufficient flow rate depending on a supply amount of the reaction gas, to thereby cause a collision of the reaction gas in the contact portion. The nozzles are provided toward an arbitrary place in the contact portion. The diameters of the nozzles may be the same or different from each other. The arbitrary place may be one place or a plurality of places.

In the present invention, the reaction gas supply devices are preferably provided toward a direction so that the reaction gas supplied from each of the reaction gas supply devices collides at one place in the contact portion for improving the dispersibility of the reaction gas in the contact portion.

The same reaction gas supply devices are used in the present invention. The reaction gas supply devices are preferably provided in the same plane (at the same height) in a contact portion having a circular cross sectional shape as a collecting tower to supply the reaction gas toward the center of the contact portion for improving the dispersibility of the reaction gas in the contact portion.

In the present invention, the collecting device preferably has no member such as a baffle board or an impingement plate for preventing a direct collision of the reaction gas supplied from the reaction gas supply devices, to thereby prevent formation of a polymerized product and realize a stable operation of the collecting device over a long period of time.

The solvent supply device is not particularly limited so long as the collecting solvent can be supplied to the contact portion. Examples of the solvent supply device include known devices used for supplying a collecting solvent in a gas-liquid contact device such as a tower top portion of a collecting tower or a showering device.

Materials for a collecting device, nozzles, and tubes connected to the nozzles are selected depending on a composition of a reaction gas or collecting solvent and temperature conditions, and are not particular limited. Stainless steels are often used as such materials, but the materials are not limited to stainless steels in the present invention. Examples of such materials include SUS 304, SUS 304L, SUS 316, SUS 316L, SUS 317, SUS 317L, SUS 327, and hastelloys. The materials may be selected corresponding to physical properties thereof to liquid from the viewpoint of corrosion resistance.

The collecting device of the present invention is used for collecting (meth)acrolein or (meth)acrylic acid from the reaction gas, but a substance collected in the collecting device of the present invention is not limited to (meth)acrolein or (meth)acrylic acid. The collecting device can be used for collecting an arbitrary component in a gas, which can be collected through gas-liquid contact, by selecting an appropriate solvent.

Hereinafter, an embodiment of the present invention will be described with reference to drawings, but the present invention is not limited thereto. FIG. 1 is a schematic diagram showing an example of a collecting device for acrylic acid as an embodiment of the present invention.

As shown in FIG. 1, the collecting device is provided with: a collecting tower main body 2; a reaction gas supply line for supplying a reaction gas 1 to the collecting tower main body 2; a solvent supply line for supplying an aqueous solution 3 as a collecting solvent to a top portion of the collecting tower main body 2; a bottom liquid discharge line for discharging a bottom liquid 4, which is the aqueous solution 3 containing a water-soluble component such as acrylic acid collected from the reaction gas 1, from the collecting tower main body 2; a gas discharge line for discharging a tower top distilled gas 5 such as steam generated in the collecting tower main body 2 from the top portion of the collecting tower main body; and a heat exchanger 6 for cooling part of the bottom liquid 4 returned to the collecting tower main body 2 through the bottom liquid discharge line. A supply position of the aqueous solution 3 in the collecting tower main body 2 from the solvent supply line is not limited to the tower top portion, and may be another position such as a tower center portion, or a plurality of positions such as the tower top portion and the tower center portion.

Figure 2:
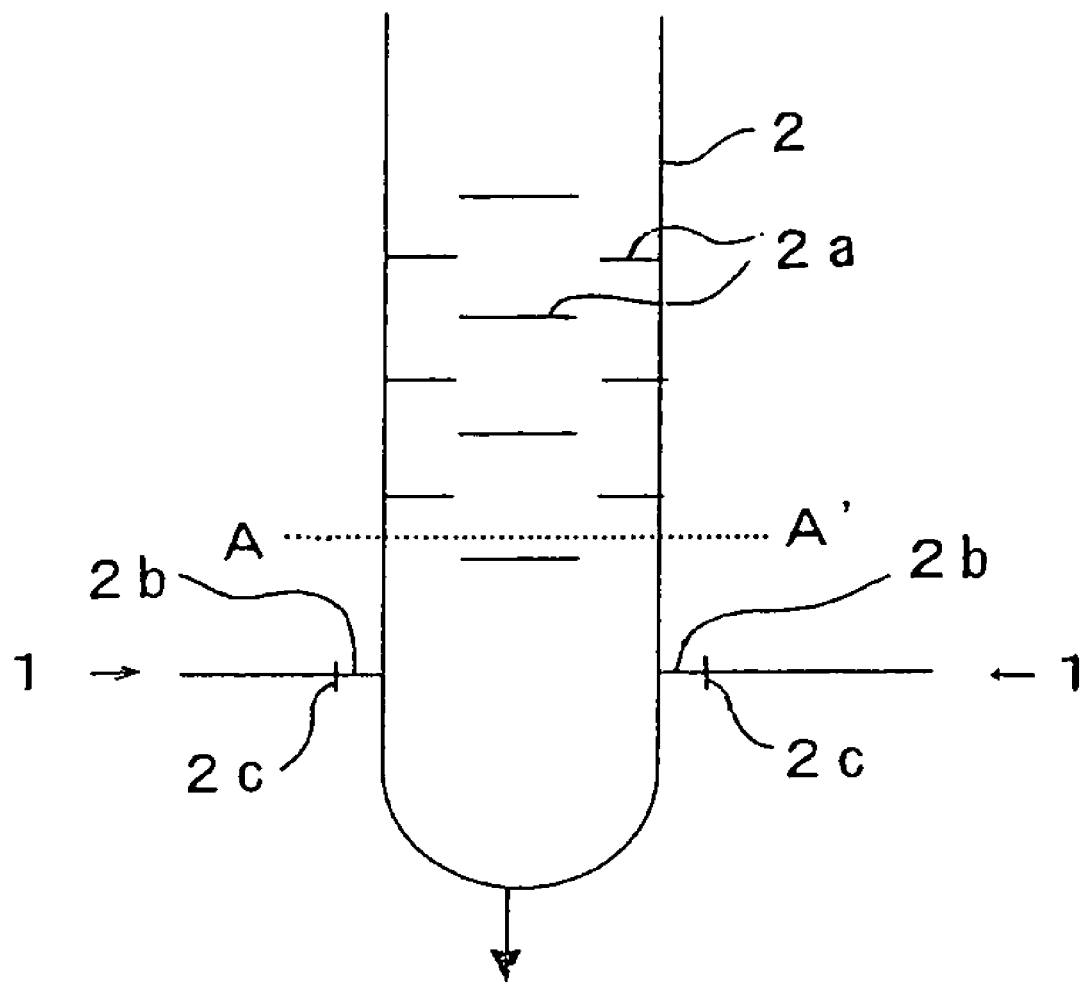
FIG. 2 is longitudinal sectional view of a bottom portion of a collecting tower main body 2 shown in FIG. 1.
Figure 3:
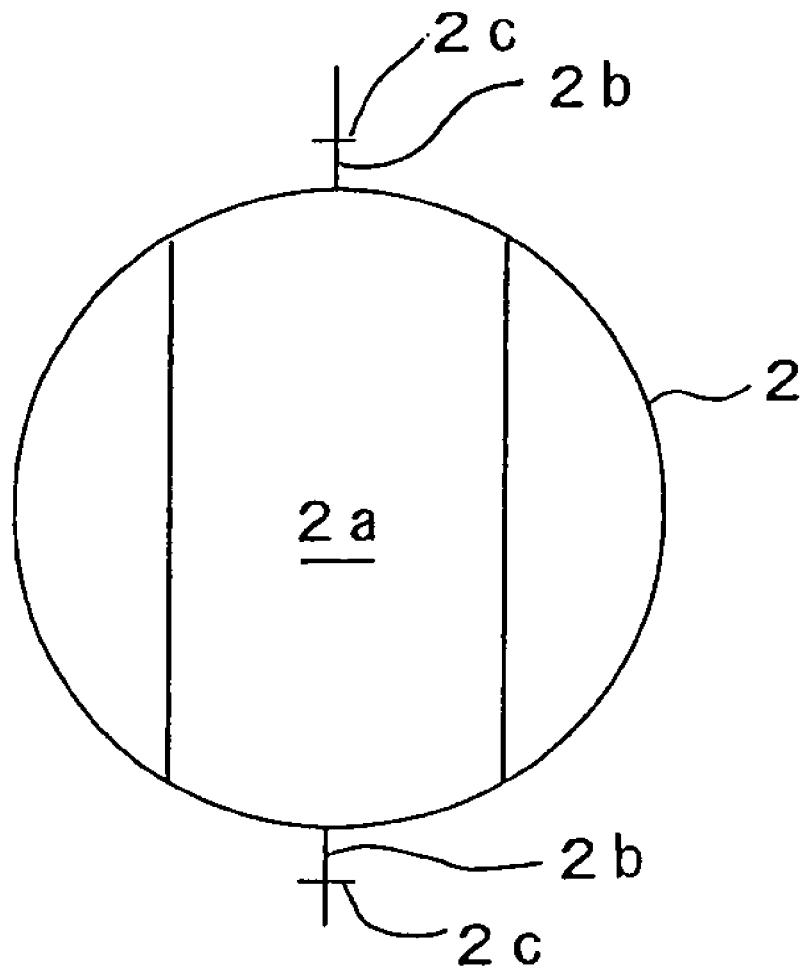
FIG. 3 is a cross sectional view showing the bottom portion of the collecting tower main body 2 taken along the line A-A' of FIG. 2 and a connecting mode of nozzles 2c connected thereto.
Figure 4:
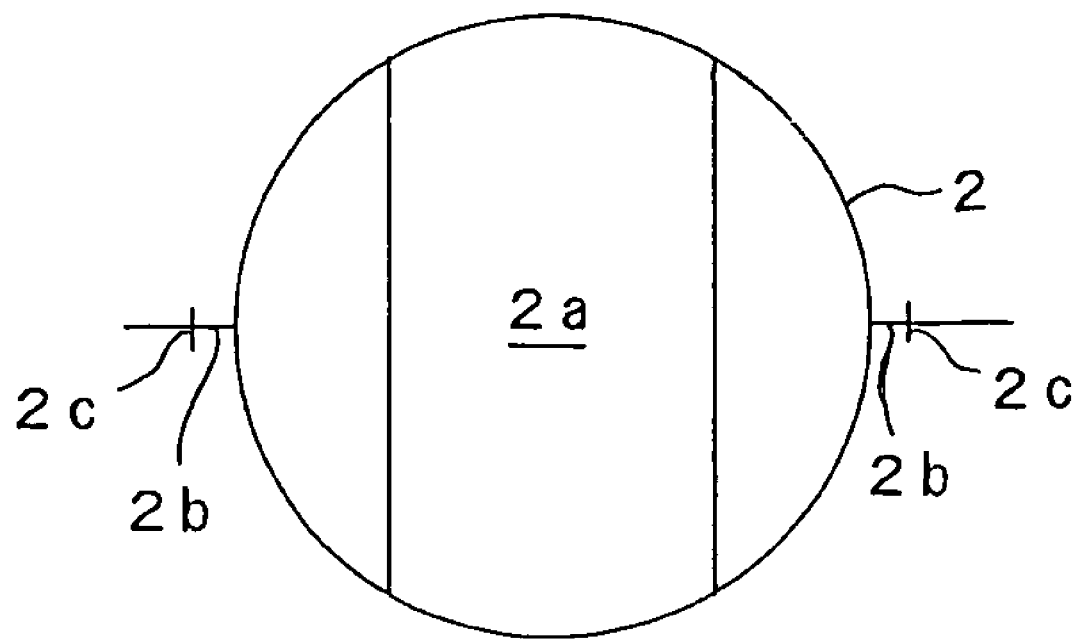
FIG. 4 is a cross sectional view showing the bottom portion of the collecting tower main body 2 taken along the line A-A' of FIG. 2 and another connecting mode of nozzles 2c connected thereto.

As shown in FIG. 2, the collecting tower main body 2 is a tray collecting tower provided with a plurality of double segment-type dual flow trays 2a. Two nozzles 2b as the reaction gas supply devices opened to a tower bottom portion are connected to the bottom portion of the collecting tower main body 2, and each of the nozzles 2b is connected to the reaction gas supply line through a flange 2c. The nozzles 2b are provided symmetrically with respect to the center of a cross section of the collecting tower main body 2. As shown in FIG. 3, the nozzles 2b are provided to face each other along a longitudinal direction of the tray 2a provided across the collecting tower main body 2 through the center thereof. Alternatively as shown in FIG. 4, the nozzles 2b are provided to face each other along a perpendicular direction of the longitudinal direction of the tray 2a.

In the collecting device, the reaction gas 1 containing acrylic acid obtained through vapor-phase catalytic oxidation is supplied to the bottom portion of the collecting tower main body 2 from an outlet of an oxidation reactor (not shown). The reaction gas 1 is cooled to preferably 140 to 250° C., particularly preferably 170 to 220° C. by a heat exchanger (not shown) provided by the outlet of the oxidation reactor or in the reaction gas supply line before being supplied to the collecting tower. If the reaction gas 1 is cooled to a temperature lower than 140° C., acrylic acid undesirably condenses in the line and polymerizes, to possibly clog tubes or the like. Too high a temperature increases a gas volume and a required amount of heat removal in the collecting tower to increase a diameter of the collecting tower. Thus, equipment expenses tend to increase while a collection efficiency tends to decrease.

When acrylic acid is produced through vapor-phase catalytic oxidation of propylene, the reaction gas 1 to be obtained generally contains acrylic acid, nitrogen, carbon dioxide, oxygen, carbon monoxide, non-condensable hydrocarbon, condensable organic substances, water, and the like. In the present invention, the term "condensable" refers to a substance when a pure substance thereof has a boiling point of 20° C. or higher.

The aqueous solution 3 as a collecting solvent is supplied to the top portion of the collecting tower main body 2. A supply temperature of the aqueous solution 3 is preferably 20 to 50° C. The aqueous solution 3 to be supplied contains 0.5 to 2 times volume of water with respect to the volume of water in the reaction gas. The supply temperature of the aqueous solution is preferably low, but is usually 20 to 50° C. A supply temperature of lower than 20° C. is not very economical because cooling by freezing equipment or the like may be costly. A supply temperature of higher than 50° C. tends to decrease the collection efficiency.

Heat removal is preferably controlled by the heat exchanger 6 provided in a periphery of the tower bottom portion to maintain a tower top temperature of the collecting tower of the tower-type collecting device within a certain range, specifically, within ±1° C. of conditions of a steady operation. By maintaining the tower top temperature within a certain range, a constant volume of water distilled (steam) from the tower top portion as the tower top distilled gas 5 can be maintained. Furthermore, a water content in an aqueous solution of acrylic acid in the tower bottom portion, that is, an acrylic acid concentration in the bottom liquid 4 can be maintained constant.

A tower bottom temperature is preferably 86° C. or lower and a tower top temperature is preferably 72° C. or lower for avoiding clogging due to polymerization of acrylic acid.

The tower top temperature may be controlled by the heat exchanger 6 alone provided in the periphery of the tower bottom portion, by a heat exchanger provided in the periphery of the tower top portion, or by the both heat exchangers.

In the present invention, the positions of the nozzles 2c are not particularly limited so long as the nozzles are arranged to cause a collision of the reaction gas 1 in the collecting tower main body 2. When the contact portion is a tray tower as shown in FIG. 1, the nozzles are preferably provided with symmetry as shown in FIGS. 3 and 4.

In the present invention, a diameter of each of the nozzles 2c is not particularly limited. A diameter of each of the nozzles 2c is usually determined by a gas flow rate in each of the nozzles 2c. The gas flow rate varies depending on the conditions such as a diameter or shape of the collecting tower main body 2 and the number of nozzles 2c provided, but is 3 to 80 m/sec., preferably 5 to 50 m/sec., more preferably 10 to 40 m/sec.

In the collecting device, the reaction gas 1 is supplied at substantially the same flow rate from the two facing nozzles 2c. The reaction gas 1 supplied to the collecting tower main body 2 from each of the nozzles 2c collides in a center portion of a cross section of the collecting tower main body 2 and disperses. In such a collecting tower main body 2, specific directional property of the reaction gas 1 is lost due to a collision of a current of the reaction gas 1. Therefore, contact between the reaction gas 1 and the aqueous solution 3 significantly enhances compared to a case without such a collision. Thus, the reaction gas 1 is efficiently absorbed in the aqueous solution 3.

In the present invention, the reaction gas 1 blown into the collecting device through the two or more nozzles 2c collides with itself and disperses, and thus, a baffle board generally provided is unnecessary.

A collecting device having one nozzle, to which the present invention is not applied, is preferably provided with a baffle board to improve the dispersibility of the gas in the collecting device, but a polymerized product forms on the baffle board. Omission of the baffle broad causes the gas to collide with a wall surface facing the nozzle and to be dispersed, but the omission is not preferable because the dispersion effect is small.

Thus, the provision of two or more nozzles as in the present invention prevents formation of a polymerized product on a baffle board. An abnormal operation caused by such a polymerized product is prevented, to thereby allow a stable operation of the collecting device over a long period of time.

The number of the nozzles 2c is 2 or more, preferably 2 to 8, more preferably 2 to 4. The number is preferably large for exhibiting the effect of the present invention, but the maximum number may be limited from industrial and economical reasons.

Acrylic acid collected in the aqueous solution as the bottom liquid 4 as described above is subjected to usual steps involved in a production method for acrylic acid. That is, acrylic acid is subjected to an extraction step for extracting an aqueous solution containing acrylic acid with an appropriate extraction solvent, a solvent separation step, a purification step, or the like, to thereby obtain purified acrylic acid.

EXAMPLES

Hereinafter, the present invention will be described in more detail with reference to examples and comparative examples, but the present invention is not limited by the examples without departing from the gist of the present invention.

Example 1

Propylene is mixed with air and an inert gas composed of water, nitrogen, and carbon dioxide. Propylene is reacted with molecular oxygen in the presence of a molybdenum oxide-based solid catalyst in a first reaction zone, to thereby obtain acrolein. Then, acrolein is reacted with molecular oxygen in the presence of a molybdenum oxide-based solid catalyst in a second reaction zone, to thereby obtain a reaction gas containing 3,200 kg/h of acrylic acid.

<1> Reaction Gas Composition

<Mole Fraction>

| | |
|---|---|
| nitrogen + carbon dioxide | 71.6% |
| non-condensed components except the above (specifically including unreacted raw material propylene, oxygen, and carbon monoxide) | 5.3% |
| acrylic acid | 6.3% |
| water | 16.4% |
| condensed components except the above (specifically including acetic acid and maleic acid) | 0.4% |

<Weight Fraction>

| | |
|---|---|
| nitrogen + carbon dioxide | 68.2% |
| non-condensed components except the above | 5.8% |
| acrylic acid | 15.2% |
| water | 10.0% |
| condensed components except the above | 0.8% |

A weight fraction of acrylic acid in the condensed components in the reaction gas was 58.5 wt %.

<2> Collecting Device

A tray collecting tower shown in FIG. 2 was used as the collecting device. As shown in FIG. 1, the collecting tower main body 2 of the collecting tower was provided with a circulation line for drawing the bottom liquid (aqueous solution containing acrylic acid as the bottom liquid 4 formed in tower bottom portion) and for circulating the liquid to the sixth tray from the bottom. The circulation line was provided with the heat exchanger 6 for cooling the circulating liquid.

The collecting tower main body 2 used in Example 1 had 36 double segment-type dual flow trays, a height of 30,000 mm, a diameter of 2,100 mm, and two reaction gas supply nozzles 2c provided at the tower bottom portion each having a diameter of 16 inches. As shown in FIG. 4, the nozzles 2c were provided symmetrically with respect to the center of the cross section of the collecting tower main body 2.

The reaction gas 1 obtained as described above was cooled to 190° C. by a heat exchanger (not shown) provided in the line from an outlet of an oxidation reactor, and was supplied to the tower bottom portion of the collecting tower main body 2 from the nozzles 2c. A gas flow rate at the nozzles 2c was about 33 m/sec.

The aqueous solution 3 at 40° C. containing 93 wt % water and 6 wt % acetic acid (the remaining 1% includes formaldehyde, formic acid, and acrylic acid) as a collecting solvent was supplied to the collecting tower main body 2 from the tower top portion, and the supply of the collecting solvent was adjusted such that a tower top pressure reached 105 kPa. The collecting solvent was supplied such that the volume of water in the collecting solvent reached the volume of water in the reaction gas. The collecting tower main body 2 was operated at a tower top temperature of 60° C. by adjusting a load of the heat exchanger 6 provided in the circulation line.

After an operation for 3 months, a loss of acrylic acid from the tower top distilled gas was 0.3% and no polymerized product was observed in the collecting tower main body 2.

Example 2

Figure 5:
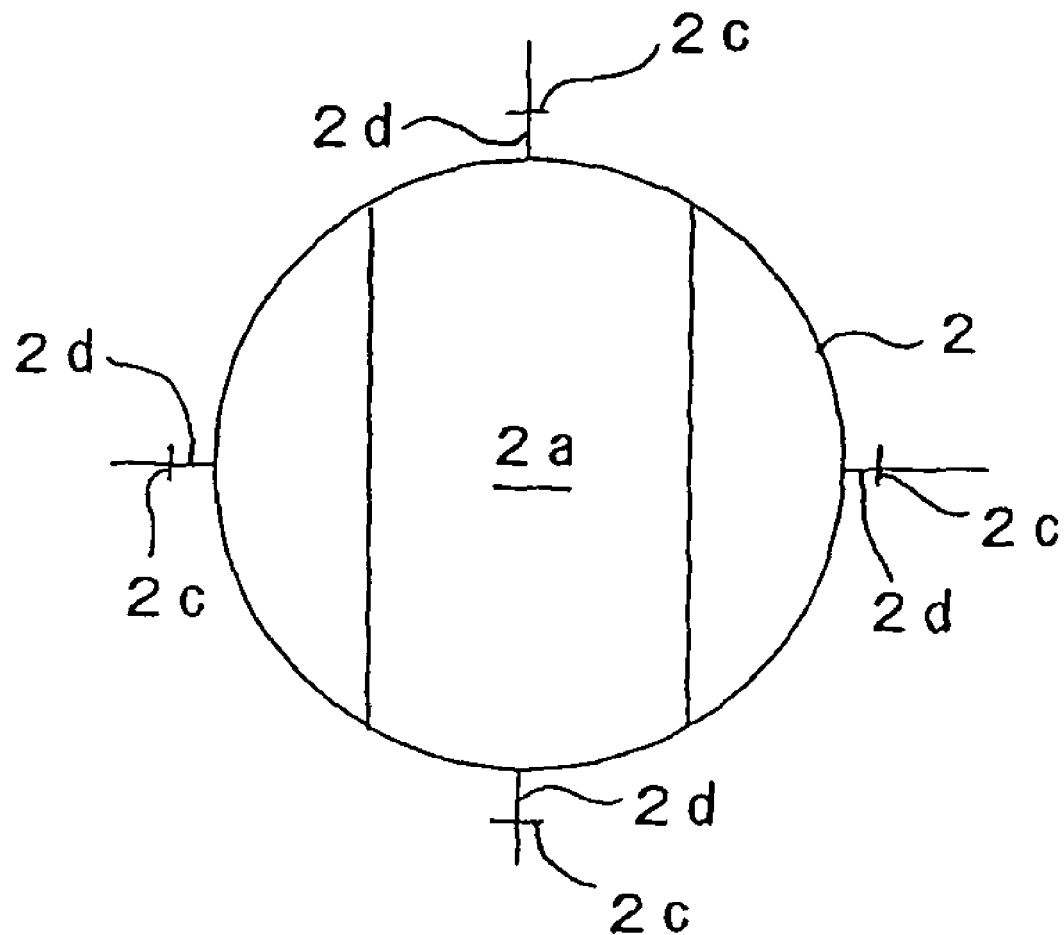
FIG. 5 is a cross sectional view of the collecting tower main body 2 showing a connecting mode of nozzles 2d in Example 2 taken along the line A-A' of the collecting tower main body 2 shown in FIG. 2.

The operation in Example 1 was repeated except that: 4 nozzles each having a diameter of 12 inches were provided at 4 symmetrical positions in the same horizontal plane so that a distance between the nozzles 2d on a cross section of the collecting tower main body 2 was equal as shown in FIG. 5; and a gas flow rate at the nozzles 2d was about 30 m/sec.

After an operation for 3 months, a loss of acrylic acid from the tower top distilled gas was 0.3%, which was the same result as in Example 1. No polymerized product was observed in the collecting tower main body 2.

Comparative Example 1

An operation in Example 1 was repeated except that: one nozzle having a diameter of 22 inches was provided at one position; and a gas flow rate at the nozzle was about 35 m/sec.

After an operation for 3 months, a loss of acrylic acid from the tower top distilled gas was 1.5%, and no polymerized product was observed in the collecting tower main body 2.

Comparative Example 2

An operation in Comparative Example 1 was repeated except that an inverted L-type vertical baffle board was provided at a tip of the nozzle in the collecting tower main body 2 for improving the dispersion of the gas.

A loss of acrylic acid from the tower top distilled gas was initially 0.4%, which was comparable to that in Example 1. However, a polymerized product was observed in the bottom liquid of the collecting tower main body 2. After 2 months, the operation was stopped, and the inside of the collecting tower main body 2 was inspected, resulting in a large amount of the polymerized product observed on the baffle board.

INDUSTRIAL APPLICABILITY

According to the present invention, the reaction gas can be further dispersed in the collecting device with enhanced contact between the reaction gas and the solvent without the use of current regulating device such as a baffle board. Thus, (meth)acrolein or (meth)acrylic acid can be efficiently collected using the solvent while preventing polymerization.

The invention claimed is:

1. A collecting device for collecting (meth)acrolein or (meth)acrylic acid from a gaseous oxidation mixture by contacting a reaction gas with a solvent, comprising:
   a contact portion where the reaction gas is brought into contact with the solvent,
   a plurality of reaction gas supply devices for supplying the reaction gas to the contact portion, and
   a solvent supply device for supplying the solvent to the contact portion, wherein
   the plurality of reaction gas supply devices are provided in directions so as to cause a direct collision of the reaction gas supplied from the respective reaction gas supply devices at one place in the contact portion,
   the (meth)acrolein or (meth)acrylic acid is contained in the reaction gas, and the reaction gas is obtained through a vapor-phase catalytic oxidation reaction of at least one selected from the group consisting of propane, propylene and isobutylene or (meth)acrolein, and molecular oxygen or a molecular oxygen-containing gas.

2. The collecting device according to claim 1, wherein the contact portion has a circular cross sectional shape and the plurality of reaction gas supply devices are provided in the same plane to supply the reaction gas toward a center of the contact portion.

3. The collecting device according to claim 1, wherein the contact portion comprises a collecting tower.

4. The collecting device according to any one of claim 1, 2 or 3, wherein no member which prevents a direct collision of the reaction gas supplied from the plurality of reaction gas supply devices is provided.

5. The collecting device according to claim 1, wherein the one place in the contact portion is substantially equidistant from the plurality of reaction gas supply devices.

6. The collecting device according to claim 1, wherein the plurality of reaction gas supply devices is one selected from the range consisting of 2 to 8.

* * * * *